(12) United States Patent
Johnson

(10) Patent No.: US 9,968,623 B2
(45) Date of Patent: May 15, 2018

(54) PREPACKAGED STERILE SYRINGE OR CONTAINERS WITH VARIOUS SUBSTANCE CONCENTRATIONS WITH OR WITHOUT BIOACTIVE REAGENT

(71) Applicant: Lanny Leo Johnson, Frankfort, MI (US)

(72) Inventor: Lanny Leo Johnson, Frankfort, MI (US)

(73) Assignee: Lanny Leo Johnson, Frankfort, MI (US)

( * ) Notice: Subject to any disclaimer, the term of this patent is extended or adjusted under 35 U.S.C. 154(b) by 0 days. days.

(21) Appl. No.: 14/014,255

(22) Filed: Aug. 29, 2013

(65) Prior Publication Data

US 2015/0065438 A1 Mar. 5, 2015

(51) Int. Cl.
| | |
|---|---|
| A61K 31/7004 | (2006.01) |
| A61K 31/352 | (2006.01) |
| A61K 9/00 | (2006.01) |
| A61K 47/26 | (2006.01) |
| A61K 31/7048 | (2006.01) |

(52) U.S. Cl.
CPC ........ *A61K 31/7004* (2013.01); *A61K 9/0019* (2013.01); *A61K 31/352* (2013.01); *A61K 31/7048* (2013.01); *A61K 47/26* (2013.01)

(58) Field of Classification Search
CPC .............. A61K 31/7004; A61K 31/352; A61K 9/0019; A61K 47/26; A61K 31/7048
USPC .................................................. 514/23, 456
See application file for complete search history.

(56) References Cited

U.S. PATENT DOCUMENTS

| | | | |
|---|---|---|---|
| 4,880,416 A | 11/1989 | Horiuchi et al. | |
| 4,997,850 A | 3/1991 | Kimura et al. | |
| 5,304,205 A | 4/1994 | Shinoda et al. | |
| 5,403,587 A | 4/1995 | McCue et al. | |
| 6,315,992 B1 | 11/2001 | Noh et al. | |
| 7,575,743 B2 | 8/2009 | Hunziker | |
| 8,236,492 B2 | 8/2012 | McDonnell et al. | |
| 8,263,069 B2 | 9/2012 | Johnson | |
| 9,486,468 B2 | 11/2016 | Johnson | |
| 2002/0058614 A1 | 5/2002 | Filvaroff et al. | |
| 2004/0105878 A1 | 6/2004 | Schwendeman et al. | |
| 2004/0127459 A1 | 7/2004 | Dehayza et al. | |
| 2004/0268425 A1* | 12/2004 | Bookbinder et al. | 800/18 |
| 2005/0055073 A1* | 3/2005 | Weber | 607/99 |
| 2006/0025354 A1 | 2/2006 | Nair et al. | |
| 2006/0040894 A1 | 2/2006 | Hunter et al. | |
| 2006/0051327 A1 | 3/2006 | Johnson | |
| 2006/0210552 A1 | 9/2006 | Demopulos et al. | |
| 2006/0234957 A1 | 10/2006 | Tsuda et al. | |
| 2006/0258588 A1 | 11/2006 | Pike et al. | |
| 2007/0020237 A1 | 1/2007 | Yoon et al. | |
| 2007/0021496 A1 | 1/2007 | Terkeltaub et al. | |
| 2008/0200559 A1 | 8/2008 | Kannar et al. | |
| 2009/0220572 A1* | 9/2009 | Deschatelets | A61K 31/00 424/427 |
| 2010/0196331 A1* | 8/2010 | Johnson | 424/93.7 |
| 2011/0236560 A1* | 9/2011 | Perlman | A23L 5/28 426/648 |

FOREIGN PATENT DOCUMENTS

JP 08104628 A 4/1996

OTHER PUBLICATIONS

Kay et al. Anthocyanin metabolites in human urine and serum. Br J Nutr 91:933-942, 2004.*
Abelson et al, "The Other Side of Antibiotics", Review of Ophthalmology ,Online Publication, Jun. 2008 <http://www.revophth.com/content/d/therapeutic.sub.--topics/i/1227/c/2-3088/>.
Ahmed et al., ECAM 2005; 2:301-8.
Ahmed et al., "Punica granatum L. extract inhibits IL-beta-induced expression of matrix metalloproteinases by inhibiting the activation of MAP kinases and NF-kappaB in human chondrocytes in vitro," J. Nutr., 135: 2096-2102 (2005).
Aldrich Catalog (1996) p. 1221.
Anderson et al., J Agric Food Chem, 2004; 52(1):65-70.
Baeurle et al., Polymer 2009; 50:1805-13.
Barbero et al., OsteoArthritis and Cartilage, 2004;12:476-84.
Bernardeau et al., Ann. Rheum. Dis., 2001; 60(5):518-20.
Buckwalter et al., J. Bone Joint Surg. Am., Apr. 1997; 79:612-32.
Bulstra et al., "The Effect in Vitro of Irrigating Solutions on Intact Rat Articular Cartilage", The Journal of Bone and Joint Surgery [BR], vol. 76-B 1994, p. 468-470.
Cai et al., Osteoarthritis Cartilage, Sep. 2002; 10(9):692-706.
Ceuninck et al., Arthritis Res Ther 2004; 6(5):R393-R403.
Chen et al., Arthritis Research and Therapy 2008; 10:223.
De Bari et al., Arthritis and Rheumatism, Aug. 2001; 44(8):1928-1942.
Dextrose definition from http://medical-dictionary.thefreedictionary.com/dextrose downloaded Feb. 20, 2014.
Dieppe et al., BMJ 2004; 329(7471):867-868.
Dieppe et al., Rheum. Dis. Clin. N. Am., 2003; 29(4):687-716.

(Continued)

*Primary Examiner* — Yih-Horng Shiao
(74) *Attorney, Agent, or Firm* — Brinks Gilson & Lione; Ryan L. Marshall; Bryan Richardson

(57) ABSTRACT

A prepackaged sterile syringe or bottle with various concentrations of tissue and organ biologically stimulating reagents i.e., dextrose, various anthocyanins, anthocyanidins and/or their various metabolites (i.e., protocatechuic acid) as the base, can be used as a product and service not otherwise available to those practicing prolotherapy. A selected bioactive agent could be added to enhance the treatment effectiveness. The prepackaged sterile syringe or bottle can be produced in standardized concentrations of reagents and can be produced in a regulated facility to meet all the government standards of oversight necessary to insure a safe sterile product of uniform nature. The prepackaged sterile syringe or bottle provides cost savings as well as enhanced quality control, time and labor efficiency at the treatment sites.

24 Claims, 2 Drawing Sheets

(56) References Cited

OTHER PUBLICATIONS

Dore et al., Arthritis and Rheutism, 1995;38(3):413-419.
Du et al., "Anthocyanins of Pomegranate, Punica granatum," J. Food Science, 40(2):417-18 (1975).
Fortier et al., J Bone and Joint Surg Mar. 2002; 84-B(2):276-288.
Frei, EurekAlert! Mar. 2007, news release by Oregon State University.
Grimberg et al., J Cell Physiol Apr. 2000; 183(1):1-9.
Grogan et al., Arthritis & Rheumatism, Feb. 2, 2007;56(2)586-95.
Guccione et al., American Journal of Public Health, 1994; 84(3):351-358.
He et al. Zhongguo Zhong Yao Za Zhi (2005): 1602-5 provided by FLS, Inc. Oct. 2011, English translation of the full paper.
Homandberg et al., Biochimica et Biophysica Acta 1996; 1317(2):143-8.
Hunziker et al., J Bone Surg [Am] 1996; 78(5):721-733.
Karlsson et al., Arthritis Research and Therapy 2009; 11:121.
Kassirer, New England Journal of Medicine Sep. 1998; 339(12):839-41.
Kay et al., Br J Nutr Jun. 2004; 91(6):933-42.
Kellner et al., J Drug Target, 2001; 9(6):439-48.
Key et al., J Bone Joint Surg Am 1925; 7:793-813.
Keyszer et al., J. Rheumatol. Feb. 1995; 22(2):271-81.
Kim et al., J Korean Acad Rehabil Med Apr. 2006; 30(2):173-178.
Kim, et al., "Mulberry Extract Supplements Ameliorate the Inflammation-Related Hematological Parameters in Carrageenan-Induced Arthritic Rats," J. Medicinal Food, 9(3):431-435 (2006).
Ledhingham et al., Annals of Rheumatic Disease, 1993; 52:520-526.
Lende, Amol B., et al., "Anti-inflammatory and analgesic activity of protocatechuic acid in rats and mice," Inflammopharmacol., 19:255-263 (2011).
Liggins, et al., "Intra-articular treatment of arthritis with microsphere formulations of paclitaxel: biocompatibility and efficacy determinations in rabbits," Inflamm. Res., 53:363-372 (2004).
Lis et al., Chir Narzadow Ruchu Ortop Pol., 2005; 70(6):407-10.
Lotito et al., Free Radic. Biol. Med., 2006; 41(12):1727-46.
Matsumoto et al., Journal of Clinical Endocrinology and Metabolism 1996; 81:150-5.
Marks, R., "Obesity Profiles with Knee Osteoarthritis: Correlation with Pain, Disability, Disease Progression," Obesity, 15(7):1867-1874 (Jul. 2007).
Matsumoto, et al., "Ingested Delphinidin-3-rutinoside Is Primarily Excreted to Urine as the Intact Form and to Bile as the Methylated Form in Rats," J. Agri. Food Chem., 54:578-582 (2006).
Matsumoto, et al., "Identification and characterization of insulin-like growth factors (IGFs), IGF-binding proteins (IGFBPs), and IGFBP proteases in human synovial fluid," Journal of Clinical Endocrinology & Metabolism, 81:150-155 (1996).
Miller et al., BMC Complimentary and Alternative Med 2006; 6:13.
Miller et al., Journal of Inflammation 2007; 4:16.
Nair et al., J Agric Food Chem, Jan. 12, 2005; 53(1):28-31.
Nakajima-Nagata et al., Biochem. Biophys. Res. Commun., 2004; 318:625-630.
Nih, Vitamin E Fact Sheet, May 2009.
O'Driscoll, Journal of Bone and Joint Surgery, 1998; 80:1795-1812.
Olsson et al., Ann Rheum Dis 2001;60:187-193.
Park, et al., " Intra-articular injection of a nutritive mixture solution protects articular cartilage from osteoarthritic progression induced by anterior cruciate ligament transection in mature rabgits: a randomized controlled trial," Arthrtis Research and Therapy, 9:R8, 9 pages online at htpp://arthritis-research/content/9/1/R8 (2007).
Pergola, C., et al., "Inhibition of nitric oxide biosynthesis by anthocyanin fraction of blackberry extract," Nitric Oxide, 15:30-39 (2006).
Reagan et al., "Irrigating Solutions for Arthroscopy", The Journal of Bone and Joint Surgery, vol. 65-A, No. 5 Jun. 1983, p. 629-631.
Reddy, et al., "Relative Inhibition of Lipid Preoxidation, Cyclooxygenase Enzymes, and Human Tumor Cell Proliferation by Natural Food Colors," J. Agri. Food Chem., 53:9268-9273 (2005).
Reeves et al., Alt Ther Hlth Med 2000; 6(2):37-46.
Reeves, et al., "Randomized Prospective Double Blind Placebo-Controlled Study of Dextrose Prolotherapy for Knee Osteoarthritis With or Without ACL Laxity," Alternative Therapies, 6(2):68-80 (2000).
Reeves et al., Alt Ther Hlth Med May-Jun. 2003; 9(3):58-62.
Reeves, J Altern Complement Med. Aug. 2000; 6(4):311-20.
Reeves, et al., "Recurrent Dislocation of Total Knee Prostheses in a Large Patient: Case Report of Dextrose Proliferant Use," Arch. Phys. Med. Rehabil., 78:1039, Poster 35 (1997).
Schmidt et al., Osteoarthitis Cartilage, May 2006; 14(5):403-12.
Schneiderman et al., Arch Biochem Biophys Dec. 1995; 324(1):173-88.
Seeram, et al., "Cyclooxygenase inhibitory and antioxidant cyanidin glycosides in cherries and berries," Phytomedicine, 8(5):362-369 (2001).
Smith et al., British Medical Journal, 2000; 321:847-48.
Strauss et al., American Journal of Sports Medicine, Aug. 2009; 37(8):1636-1644.
Thakkar, et al., "Efficacy of chitosan microspheres for controlled intra-articular delivery of celecoxib in inflamed joints," J. Pharmacy Pharmacology, 56:1091-1099 (2004).
The six types of synovial joints from http://www.ask.com/question/six-types-of-synovial-joints downloaded Feb. 20, 2014.
Tucker, M., "Lidocaine Contact Allergy Increasing with Topical Use," (2007) from http://www.acept/Content.aspx?d=26848, downloaded Jul. 10, 2014.
Torskangerpoll et al., Food Chem., 89:427-440 (2005).
Uitterlinden et al., BMC Musculoskeletal Disorders 2008; 9:120.
Wang, J., et al., "Inhibitory Effects of Anthocyanins and Other Phenolic Compounds on Nitric Oxide Production in LPS/IFN-y-Activated RAW 264.7 Macrophages," J. Agric. Food Chem., 50:850-857 (2002).
Wang et al., J. Agric. Food Chem. 1997,45:304-9.
Woodward et al., J. Agric. Food Chem. 2009; 57:5271-78.

\* cited by examiner

PREPACKAGED STERILE SYRINGE OR CONTAINERS WITH VARIOUS SUBSTANCE CONCENTRATIONS WITH OR WITHOUT BIOACTIVE REAGENT

BACKGROUND OF THE INVENTION

The present invention relates to medications and, more particularly, to a prepackaged syringe or container, such as a vial, containing a predetermined and premeasured concentration of a substance, such as dextrose, anthocyanins, anthocyanidins and/or their metabolites, optionally including one or more bioactive reagents.

Prolotherapy is also known as "proliferation therapy," "regenerative injection therapy," or "proliferative injection therapy". It involves injecting an otherwise non-pharmacological and non-active irritant solution into the body, generally in the region of tendons or ligaments for the purpose of strengthening weakened connective tissue and alleviating musculoskeletal pain.

Prolotherapy was originally hypothesized to reinitiate the inflammatory process that deposits new additional fibers thereby repairing lax tendons or ligaments and to possibly promote the release of local growth factors. Once strengthened, the weak areas would no longer send pain signals.

Subsequently, reports of physiological changes to synovial joints have been reported following dextrose intra-articular injection. (Reeves K D, Hassanein K: Randomized prospective double blind placebo controlled study of dextrose prolotherapy of knee osteoarthritis with and without ACL laxity. Alt Ther Hlth Med 2000;6(2):37-46. Reeves K D, Hassanein K: Randomized prospective double blind placebo controlled study of dextrose prolotherapy of osteoarthritic thumbs and finger (DIP, PIP and trapeziometacarpal joints) Evidence of Clinical Efficacy. Jnl Alt Compl Med 2000;6(4):311-320. Reeves K D, Hassanein K: Long term effects of dextrose prolotherapy for anterior cruciate ligament laxity: A prospective and consecutive patient study. Alt Ther Hlth Med 2003;9(3)58-62.)

These results were without explanation at the time. Referring to FIGS. 3 and 4, subsequent proof of principle studies on human synovial explants by the applicant showed that various levels of dextrose resulted in the human synovium producing insulin stimulating growth hormone (IGF-1) and turning the gene on for same. The low glucose in medium was 1 gram glucose per liter and the higher dose was 4.5 grams of glucose per liter in the culture media.

These observations suggested that the dextrose injection was not just a sclerosing agent as previously proposed, but one that incited the local tissues to produce a growth hormone(s). There is medical literature support for this concept. (Murphy M, Godson C, Cannon S, Kato S, Mackenzie H S, Martin F, Brady H R. Suppression Subtractive Hybridization Identifies High Glucose Levels as a Stimulus for Expression of Connective Tissue Growth Factor and Other Genes in Human Mesangial Cells. J Bio Chem, 274, 5830-5834.) They reported that that the tissue glucose was 0.1% and the injection raised the level to 0.45%. Within 20 minutes of the glucose injection there were fifteen different proteins identified including connective tissue growth factor (CTGF) and transforming growth factor beta (TGF-$\beta$1).

Armed with the in vitro study results, a proof of principle clinical trial was performed on 6 subjects. They all had radiological imaging evidence of exposed bone on medial compartment of the knee joint. They had arthroscopic inspection and video documentation of their lesion. The video records were libraried for subsequent comparison. They were given monthly injections of 9 cc or 12.5% dextrose. Subsequently arthroscopic inspection between 8 and 12 months showed the regrowth of articular cartilage in area previously denuded. Biopsy of these areas showed hyaline cartilage, supported by histochemical characteristics and type II collagen.

Prolotherapy has rapidly expanding indications based upon clinical results. Its use in arthritic joints has been reported. (Murphy M, Godson C, Cannon S, Kato S, Mackenzie H S, Martin F, Brady H R. Suppression Subtractive Hybridization Identifies High Glucose Levels as a Stimulus for Expression of Connective Tissue Growth Factor and Other Genes in Human Mesangial Cells. J Bio Chem, 274, 5830-5834.) (Dumais R, Benoit C, Dumais A, Babin L, Bordage R, deArcos C, Allard J, Belanger. Effect of Regenerative Injection Therapy on Function and Pain in Patients with Knee Osteoarthritis: A Randomized Crossover Study. Pain Medicine 2012 Jul. 3. doi: 10.1111/j.1526-4637.2012.01422.x. [Epub ahead of print]) (Rabado D, Zgierska A, Fortney L, Kijowski R, Mundt M, Ryan M, Grettie J, Patterson J J. Hypertonic dextrose injections (prolotherapy) for knee osteoarthritis: results of a single-arm uncontrolled study with 1-year follow-up. J Altern Complement Med. 2012 April;18(4):408-14.)

Dextrose prolotherapy injections have been used for Osgood Slater's Disease, a non union of bone at the tibial tubercle. (Topol G A, Podesta L A, Reeves K D, Raya F, Fullerton D B, Yeh H. Hyperosmolar Dextrose Injection for Recalcitrant Osgood-Schlatter Disease. Pediatrics. 2011 November;128(5) 121-8.; originally published online Oct. 3, 2011).

Prolotherapy was popularized in the 1950's. (Hackett G S. Ligament and Tendon Relaxation treated by Prolotherapy: 1st edition 1956). It is practiced by thousands of health care providers at this time. The practice includes injections of both intra-articular and various extra articular tissues.

The ancient practice of each practitioner mixing their own concentrations of reagents has not changed since the conception. The commonly used material is dextrose liquid of a percent greater than physiologic. This requires each practitioner to purchase separately the containers or syringes. They must buy the dextrose and the vehicle, such as normal (0.9%) saline, Ringer's lactate solution, or the like. They then must mix at their location. This is labor intensive and inefficient. The practitioner often adds other reagents that would enhance a tissue reaction, but not one that would be known to promote growth hormone production. This conventional method does not insure or validate sterility. Moreover, this conventional method lacks standardization and the concentration of dextrose delivered can vary depending on the accuracy of the person mixing the various components. Finally, the shelf life of the components is not reliable or standardized.

There is currently no commercially available, prepackaged product to facilitate the process, insure sterility and uniform concentrations of dextrose, various anthocyanins, anthocyanidins, their metabolites, and/or bioreactive reagent(s).

As can be seen, there is a need for a prepackaged syringe or container, such as a vial, containing a predetermined and premeasured substance, such as dextrose, anthocyanins, anthocyanidins, or the like, in a desired concentration, optionally including one or more bioactive reagents.

SUMMARY OF THE INVENTION

In one aspect of the present invention, a kit for prolotherapy, the kit comprises a container filled with a solution for injection in prolotherapy; and a sterile packaging holding the container therein.

In another aspect of the present invention, a method for practicing prolotherapy comprises providing a prolotherapy kit to a practitioner, the kit including a container filled with a solution for injection in prolotherapy, and a sterile packaging holding the container therein; removing the container from the sterile packaging; and injecting an effective amount of the solution to a patient in need thereof.

In a further aspect of the present invention, a method for the treatment of synovial joint injury or disease by administering an effective amount of a prolotherapy solution to a patient in need thereof comprise providing a prolotherapy kit to a practitioner, the kit including a container filled with a solution for injection in prolotherapy, and a sterile packaging holding the container therein; removing the container from the sterile packaging; and injecting an effective amount of the solution to a patient in need thereof.

In a further aspect of the present invention, a method for the treatment of joints, bones, and soft tissue injury or disease by administering an effective amount of a prolotherapy solution to a patient in need thereof comprise providing a prolotherapy kit to a practitioner, the kit including a container filled with a solution for injection in prolotherapy, and a sterile packaging holding the container therein; removing the container from the sterile packaging; and injecting an effective amount of the solution to a patient in need thereof.

In a further aspect of the present invention, a method for the treatment of pain by administering an effective amount of a prolotherapy solution to a patient in need thereof comprise providing a prolotherapy kit to a practitioner, the kit including a container filled with a solution for injection in prolotherapy, and a sterile packaging holding the container therein; removing the container from the sterile packaging; and injecting an effective amount of the solution to a patient in need thereof.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a prepackaged sterile syringe or bottle with various concentrations of tissue and organ biologically stimulating reagents i.e., dextrose, various anthocyanins, anthocyanidins and/or their various metabolites (i.e., protocatechuic acid) as the base, can be used as a product and service not otherwise available to those practicing prolotherapy. A selected bioactive agent could be added to enhance the treatment effectiveness. The prepackaged sterile syringe or bottle can be produced in standardized concentrations of reagents and can be produced in a regulated facility to meet all the government standards of oversight necessary to insure a safe sterile product of uniform nature. The prepackaged sterile syringe or bottle provides cost savings as well as enhanced quality control, time and labor efficiency at the treatment sites.

Figure 1:
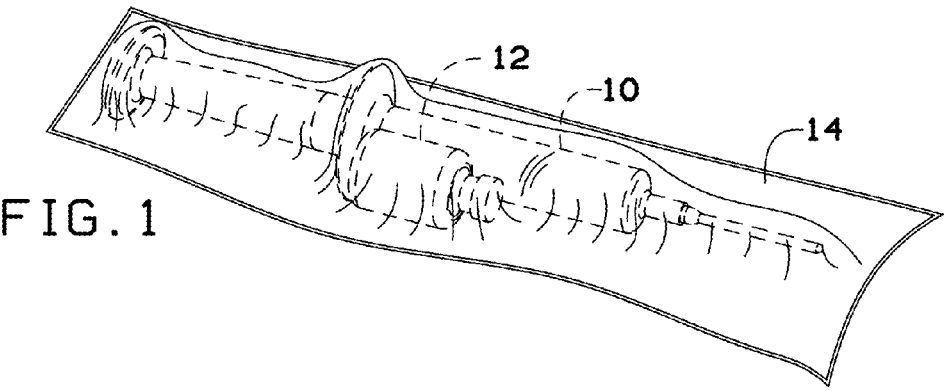
FIG. 1 is a perspective view of a prepackaged syringe and vial according to an exemplary embodiment of the present invention.

Referring to FIG. 1, in some embodiments of the present invention, a syringe 10 and/or a bottle 12 can be packaged in a sterile packaging 14. While FIG. 1 shows both a syringe 10 and a bottle 12 in the sterile packaging 14, in some embodiments, a pre-filled, capped syringe could only be disposed inside the sterile packaging 14, or only the bottle 12 (pre-filled) could be disposed inside the sterile packaging 14 and, in this embodiment, the user would use their own sterile, prepackaged syringe to draw the pre-filed solution from the bottle 12.

The sterile packaging 14 contains a dextrose solution, a solution of an anthocyanin, a solution of an anthocyanidin, or various metabolites of the same, in a predetermined concentration. This concentration can be labeled on the sterile packaging 14 so that a user can easily know that, when they open the sterile packaging 14, that they are obtaining the desired substance, made to specific standards and in a regulated facility, such as a facility practicing good manufacturing practices (GMP) and/or good laboratory practices (GLP).

Figure 2:
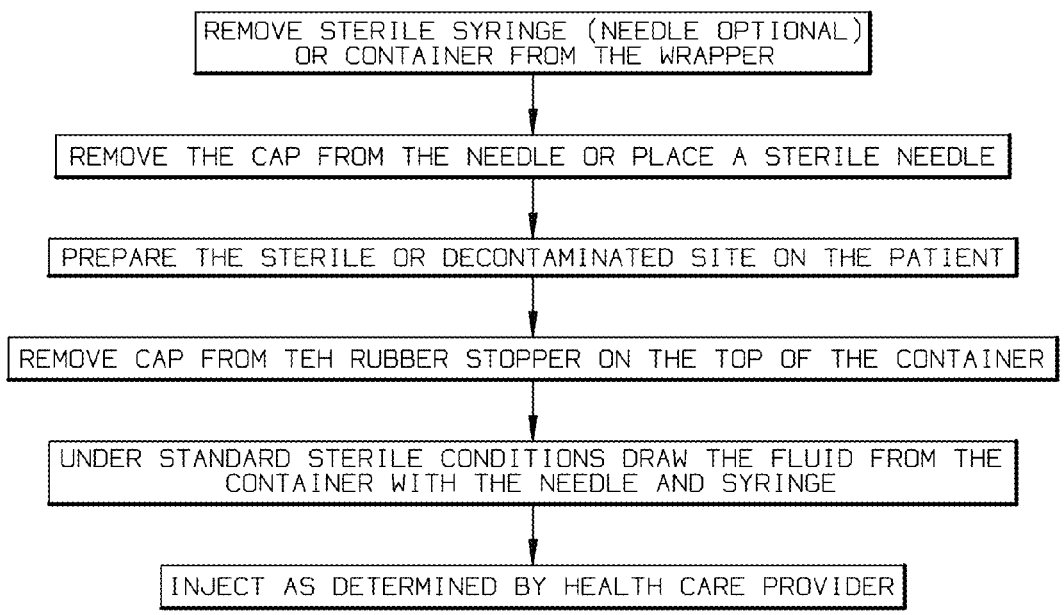
FIG. 2 is a flow chart describing an exemplary method for practicing prolotherapy, according to an exemplary embodiment of the present invention.
Figure 3:
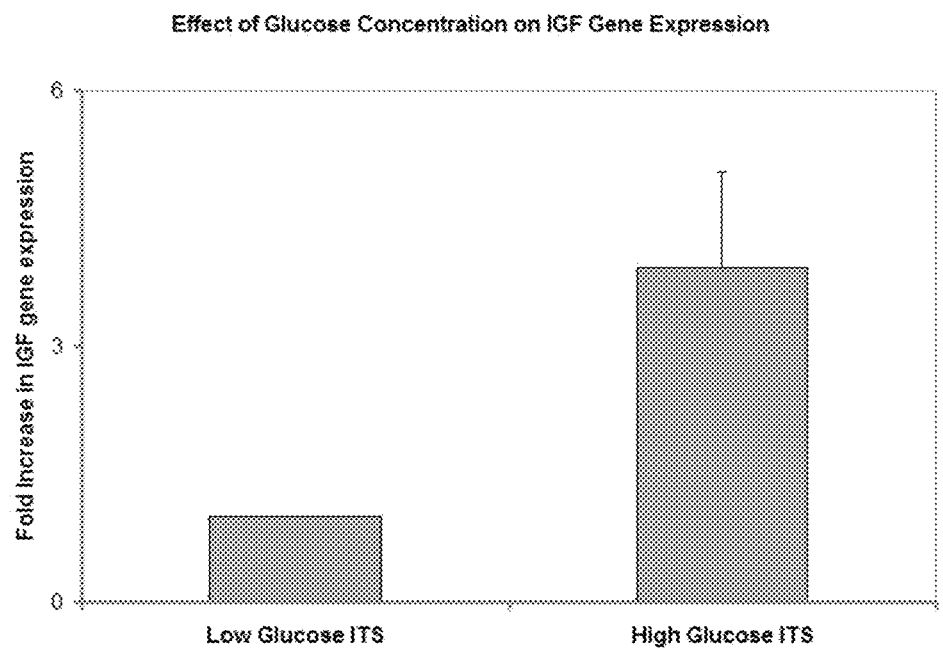
FIG. 3 is a graph showing the effect of glucose concentration on IGF gene expression.
Figure 4:
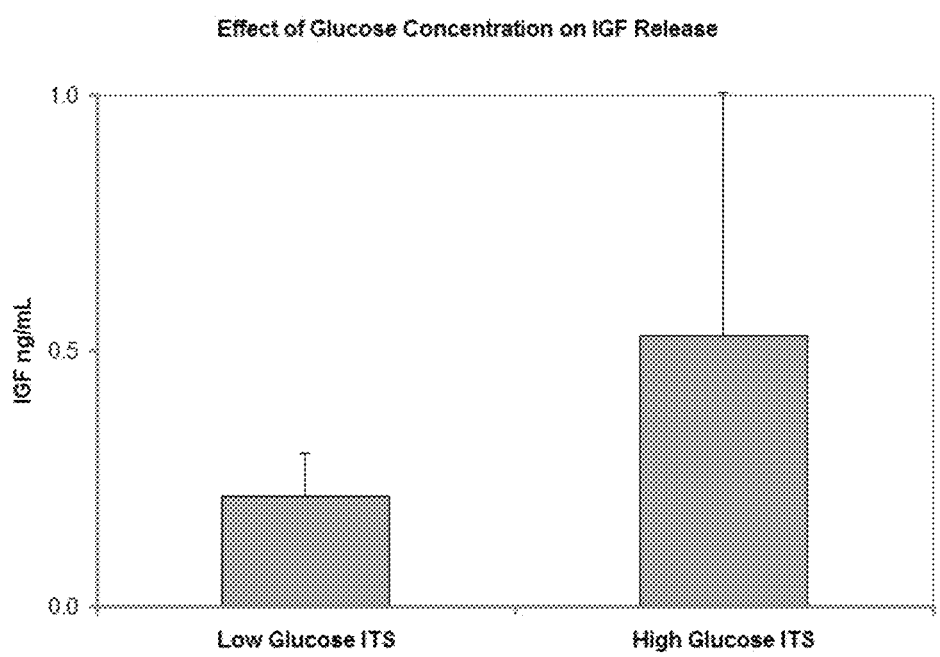
FIG. 4 is a graph showing the effect of glucose concentration on IGF release.

Referring now to FIG. 2, to practice the methods of the present invention and use the prepackaged, pre-filled, pre-measured product of the present invention, a user first would remove the sterile syringe 10 or container 12 from the sterile packaging 14. The syringe 10 or the container 12 can be pre-filled with the product, ready to use. When product is provided in a pre-filled syringe, the syringe 10 could be capped or may include a syringe on the end thereof. The plunger may be held in place with a breakaway seal that can be broken at the time of use, but prevents depression of the plunger while in its packaging. When product is provided in a pre-filled container 12, the container 12 can include, for example, cap covering a septum that a needle can be inserted into to access the contents. The sterile packaging 14 can include, for example, a peel-away paper or plastic backing that can retain sterility of the contents, while being easily removed therefrom.

Next, when the product is provided in a syringe, the practitioner can remove the cap from the needle or can remove the cap from the syringe and place on a sterile needle. When the product is provided in a container, the practitioner can remove the cap from the rubber stopper (septum) on the top of the container and, under standard sterile conditions, draw the fluid from the container with a needle and syringe. As discussed above, in some embodiments, the practitioner can use their own syringe. In other embodiments, an empty syringe can be provided with the container having the product therein, providing a syringe and product in a single, convenient, sterile packaging.

The practitioner can then prepare the sterile or decontaminated site on the patient, where the injection site is chosen by the practitioner and the site appropriate cleaned prior to needle injection. When ready, the practitioner can inject the product into the recipient, with the knowledge that the product injected is of a known, accurate concentration and is being delivered in a clean, sterile, and safe manner.

As described above, the pre-filled product in the syringe or the container can include a prolotherapy agent (such as dextrose in a concentration greater than physiological, a solution of an anthocyanin, a solution of an anthocyanidin, or various metabolites of the same,) and one or more bioactive agents. The bioactive agents can be those that could enhance a tissue reaction, but not one that would be known to promote growth hormone production.

Embodiments of the present invention can include both apparatus and method embodiments. An apparatus according to an exemplary embodiment of the present invention could include a pre-filled, prepackaged, sterile container, which may be a syringe, vial or the like, that is filled with a product ready for use in prolotherapy. This product is typically a dextrose solution, a solution of an anthocyanin, a solution of an anthocyanidin, or various metabolites of the same, at a given, predetermined and accurate concentration. In some embodiments, the prefilled vial may contain a set amount of a solid product, where the vehicle to make a solution can be separately provided by the user.

A method according to an exemplary embodiment of the present invention can include a method for delivering a prolotherapy agent, where the steps including opening a prepackaged, sterile, product pre-filled container having a given, accurate concentration, and delivering an effective amount the product to a patient in need thereof.

As used herein, an "effective amount" of a product can be an amount of product that can cause a desired effect. In prolotherapy, an effective amount can be, for example, an amount capable of reinitiate the inflammatory process of the patient.

A "patient in need thereof" can be any patient that could benefit from prolotherapy. This includes patients experiencing chronic pain, tendonitis, lateral epicondylosis, or the like.

While the present invention described the product in the container as typically being dextrose, various anthocyanins, various anthocyanidins, or various metabolites of the same, or other agents known to be useful in prolotherapy, can be provided in the pre-filled containers. These agents include, for example, glycerin, lidocaine, phenol, and sodium morrhuate, or the like.

It should be understood, of course, that the foregoing relates to exemplary embodiments of the invention and that modifications may be made without departing from the spirit and scope of the invention as set forth in the following claims.

What is claimed is:

1. A prolotherapy kit for the sterile storage and shipment of a solid prolotherapy product to create an on-site sterile prolotherapy solution, consisting of: a vial containing a predetermined amount of a solid form first bioactive agent, which is protocatechuic acid; optionally a second bioactive agent that promotes prolotherapy; optionally a vehicle for making a solution of the solid form first bioactive agent, the second bioactive agent, or the combination of the first and the second bioactive agents; optionally a sterile syringe; and a sterile package having a sterile interior housing the vial, optionally the second bioactive agent, optionally the vehicle, and optionally the sterile syringe, wherein the sterile package is sealed from the outside atmosphere.

2. The prolotherapy kit of claim 1, wherein a concentration is labelled on the sterile package indicating the predetermined amount of the protocatechuic acid and optionally indicating the predetermined amount of the second bioactive agent.

3. The prolotherapy kit of claim 2, wherein the concentration label indicates at least one liquid vehicle volume to add into the vial, based upon the predetermined amount of the protocatechuic acid and optionally the second bioactive agent, to create a desired concentration of the sterile prolotherapy solution.

4. A prolotherapy kit for the sterile storage and shipment of a solid prolotherapy product to create an on-site sterile prolotherapy solution, consisting of: a vial containing (a) a predetermined amount of a solid form first bioactive agent, which is protocatechuic acid; and optionally (b) a predetermined amount of a second bioactive agent that promotes prolotherapy; optionally a vehicle for making a solution of the solid form first bioactive agent and optionally the second bioactive agent; optionally a sterile syringe; and a sterile package having a sterile interior housing the vial, optionally the vehicle, and optionally the sterile syringe, wherein the sterile package is sealed from the outside atmosphere.

5. The prolotherapy kit of claim 4, wherein a concentration is labelled on the sterile package indicating the predetermined amount of protocatechuic acid and optionally indicating the predetermined amount of the second bioactive agent.

6. The prolotherapy kit of claim 5, wherein the concentration label indicates at least one liquid vehicle volume to add into the vial, based upon the predetermined amount of the protocatechuic acid and optionally the predetermined amount of the second bioactive agent, to create desired concentration of the sterile prolotherapy solution.

7. The prolotherapy kit of claim 4, wherein the sterile package houses a sterile syringe.

8. A method for the sterile storage and shipment of the prolotherapy kit of claim 1 from a regulated facility to an application location for the local creation or injection of a sterile prolotherapy solution, comprising: placing a predetermined amount of a solid form protocatechuic acid and optionally a predetermined amount of a second bioactive agent that promotes prolotherapy in a vial at the regulated facility; sealing the vial, optionally at least one vehicle for making a solution of the solid form first bioactive agent, the second bioactive agent, or the combination of the first and the second bioactive agents, and optionally a sterile syringe from the outside atmosphere within a sterile interior of a sterile package at the regulated facility; shipping the sterile package from the regulated facility to the application location.

9. The method of claim 8, further including the steps of withdrawing the sterile prolotherapy solution from the vial into the sterile syringe, and injecting the solution from the sterile syringe into a patient for prolotherapy.

10. The method of claim 8, wherein a concentration is labelled on the sterile package indicating a predetermined liquid vehicle volume to add into the vial, based upon the predetermined amount of the protocatechuic acid and optionally the predetermined amount of the second bioactive agent, to create the sterile prolotherapy solution.

11. The prolotherapy kit of claim 1, wherein the second bioactive agent is a sugar-free bioactive agent.

12. The prolotherapy kit of claim 1, wherein the second bioactive agent is a solid form bioactive agent.

13. The prolotherapy kit of claim 1, wherein the second bioactive agent is a non-flavonoid bioactive agent.

14. The prolotherapy kit of claim 1, wherein the second bioactive agent comprises glycerin.

15. The prolotherapy kit of claim 1, wherein the second bioactive agent comprises lidocaine.

16. The prolotherapy kit of claim 1, wherein the second bioactive agent comprises phenol.

17. The prolotherapy kit of claim 1, wherein the second bioactive agent comprises morrhuate.

18. The prolotherapy kit of claim 1, wherein the second bioactive agent comprises dextrose.

19. The prolotherapy kit of claim 1, wherein the second bioactive agent is present.

20. The prolotherapy kit of claim 4, wherein the second bioactive agent is present.

21. The prolotherapy kit of claim 20, wherein the second bioactive agent is a solid form bioactive agent.

22. The method of claim 8, wherein the second bioactive agent is present.

23. The method of claim 22, wherein the second bioactive agent is a solid form bioactive agent.

24. The prolotherapy kit of claim 1, wherein the vehicle is present.

\* \* \* \* \*